US010271811B2

(12) United States Patent
Lu et al.

(10) Patent No.: US 10,271,811 B2
(45) Date of Patent: Apr. 30, 2019

(54) SCATTER SIMULATION WITH A RADIATIVE TRANSFER EQUATION USING DIRECT INTEGRAL SPHERICAL HARMONICS METHOD FOR COMPUTED TOMOGRAPHY

(71) Applicant: TOSHIBA MEDICAL SYSTEMS CORPORATION, Otawara-shi (JP)

(72) Inventors: Yujie Lu, Vernon Hills, IL (US); Yu Zou, Naperville, IL (US); Xiaolan Wang, Buffalo Grove, IL (US); Zhou Yu, Wilmette, IL (US); Richard Thompson, Hawthorn Woods, IL (US)

(73) Assignee: TOSHIBA MEDICAL SYSTEMS CORPORATION, Otawara-shi (JP)

(*) Notice: Subject to any disclaimer, the term of this patent is extended or adjusted under 35 U.S.C. 154(b) by 273 days.

(21) Appl. No.: 15/210,657

(22) Filed: Jul. 14, 2016

(65) Prior Publication Data
US 2018/0014806 A1 Jan. 18, 2018

(51) Int. Cl.
*A61B 6/00* (2006.01)
*A61B 6/03* (2006.01)

(52) U.S. Cl.
CPC ............ *A61B 6/5282* (2013.01); *A61B 6/032* (2013.01); *A61B 6/483* (2013.01); *A61B 6/583* (2013.01); *A61B 6/4435* (2013.01)

(58) Field of Classification Search
CPC .................................................. A61B 6/5282
See application file for complete search history.

(56) References Cited

U.S. PATENT DOCUMENTS

| | | | |
|---|---|---|---|
| 6,256,367 B1 | 7/2001 | Vartanian | |
| 2001/0032053 A1 | 10/2001 | Hielscher et al. | |
| 2004/0030255 A1* | 2/2004 | Alfano | A61B 5/0073 600/476 |
| 2006/0259282 A1 | 11/2006 | Failla et al. | |

(Continued)

OTHER PUBLICATIONS

A.P. Colijn, et al, "Accelerated Simulation of Cone Beam X-Ray Scatter Projections", IEEE Transactions on Medical Imaging, vol. 23, No. 5, May 2004.

(Continued)

*Primary Examiner* — Dani Fox
(74) *Attorney, Agent, or Firm* — Oblon, McClelland, Maier & Neustadt, L.L.P.

(57) ABSTRACT

A method and apparatus is provided to calculate scatter using a method to determine primary X-ray flux, first-scatter flux, and multiple-scatter flux using an integral formulation of a radiative transfer equation and using spherical-harmonic expansion. The integral for the primary X-ray flux does not include a spherical-harmonic expansion. The integral for the first-scatter flux includes an angle-dependent scatter cross-section. The integral for the multiple-scatter flux is performed iteratively, includes spherical harmonics, and includes a scatter cross-section expanded using Legendre polynomials. The integrals of attenuation along propagation rays can be accelerated using material decomposition of the attenuation coefficients. An anti-scatter-grid term can be included in the integrals to account for the effects of an anti-scatter grid on the fluxes prior to detection of the X-rays.

20 Claims, 3 Drawing Sheets (56) References Cited

U.S. PATENT DOCUMENTS

2010/0208964 A1   8/2010   Wiegert et al.
2012/0207370 A1*  8/2012   Fahimian .............. A61B 6/032
                                                      382/131

OTHER PUBLICATIONS

Genevieve Jarry, et al. Characterization of scattered radiation of kV CBCT images using Monte Carlo simulations, Med. Phys. 33 (11), Nov. 2006, 2006 Am. Assoc. Phys. Med.

Yiannis Kyriakou, et al., "Combining deterministic and Monte Carlo calculations for fast estimation of scatter intensities in CT", Institute of Physics Publishing, Physics in Medicine and Biology, Phys. Med. Biol. 51 (2006) 4567-4568.

Wojciech Zbijewski, et al, "Efficient Monte Carlo Based Scatter Artifact Reduction in Cone-Beam Micro-CT", IEEE Transactions on Medical Imaging, vol. 25, No. 7, Jul. 2006.

G. Poludniowski et al, "An efficient Monte Carlo-based algorithm for scatter correction in keV cone-beam CT", Joint Department of Physics, Institute of Cancer Research and Royal Marsden NHS Foundation Trust, Downs Road, Sutton, Surrey, SM2 5 PT UK.

Mingshan Sun, et al, "Rapid Scatter Estimation for CBCT using the Boltzmann Transmport Equation", Medical Imaging 2014: Physics of Medical Imaging, edited by Bruce R. Whiting, et al., Proc. of SPIE vol. 9033, 2014 SPIE.

K. Franklin Evans, "The Spherical Harmonics Discrete Ordinate Method for Three-Dimensional Atmospheric Radiative Transfer", Program in Atmospheric and Oceanic Sciences, University of Colorado, Boulder, Colorado (Manuscript received Jul. 10, 1996, in final form Jun. 30, 1977), 1998 American Meterological Society.

Chuanyu Zhou et al, "Intergral-transport-based deterministic brachytherapy does calculations", Institute of Physics Publishing, Physics in Medicine and Biology, Phys. Med. Biol. 48 (2003) 73-93, Center for Nondestructive Evaluation, Iowa State University, Applied Sciences Complex II, Received May 30, 2002, Published Dec. 16, 2002, Online at stacks.iop.org/PMB/48/73, 2003 IOP Publishing Ltd.

* cited by examiner

SCATTER SIMULATION WITH A RADIATIVE TRANSFER EQUATION USING DIRECT INTEGRAL SPHERICAL HARMONICS METHOD FOR COMPUTED TOMOGRAPHY

FIELD

This disclosure relates to scatter correction of X-ray projection data, and, more particularly, to calculating scatter using a method to determine primary flux, first-scatter flux, and multiple-scatter flux using an integral formula for a radiative transfer equation and using spherical-harmonic expansions.

BACKGROUND

In general, an X-ray projection image contains many scattered radiation components. This scattered radiation can degrade the accuracy of computed tomography (CT) projection data for three-dimensional imaging using a two-dimensional detector. A two-dimensional detector, like a flat-panel detector used in an X-ray diagnostic apparatus, can use a scattered-radiation-removing grid (e.g., an anti-scatter grid) to suppress scattered radiation. The suppression of scattered radiation can be further improved by post processing the projection data using a scatter-correction algorithm. Scattered radiation correction can be advantageous for extracting low-contrast information, e.g., for imaging soft tissue, by using three-dimensional imaging using a two-dimensional detector.

An X-ray beam in the presence of a scattering object can be modeled as a primary X-ray beam $P(x, y)$ and a scattered X-ray beam $S(x, y)$, wherein the projection data $T(x, y)$ is a composite of these two:

$$T(x,y) = P(x,y) + S(x,y).$$

To correct for the scatter, a kernel-based method can be used. Alternatively, a scatter simulation can be used to compute the scatter based on information of the intervening object responsible for the scatter. Given the simulated scatter, the measured projection data can be corrected by subtracting the simulated scatter, leaving the primary beam for CT reconstruction of an image.

Inefficient scatter simulation and compensation significantly affects imaging quality including poor image contrast, artifact generation, and large errors in CT projection data. In cone-beam CT with a-wide beam geometry, scatter correction can become even more important for reconstructing high quality images. Besides hardware-based scatter rejection, such as anti-scatter grids and air gaps, approximated-convolution models with experimental parameter calibration are common in current commercial CT. However, for practical clinical applications, significant errors (typical 20-40 HU) persist when performing scatter correction using approximated-convolution models. Improved methods of correcting scatter in X-ray CT are desired.

BRIEF DESCRIPTION OF THE DRAWINGS

A more complete understanding of this disclosure is provided by reference to the following detailed description when considered in connection with the accompanying drawings, wherein.

DETAILED DESCRIPTION

Scatter correction with precise simulation of the scatter physical process using, e.g., Monte Carlo methods can reduce errors in corrected computed tomography (CT) projection data to mitigate artifacts in images reconstructed from the CT projection data. Monte Carlo methods are challenging to apply to practical scatter correction because they require significant computational resources and time. Additionally, although Monte Carlo methods can be accelerated by reducing simulated photon number and fitting the simulated data, noise from the discrete, as opposed to continuous, nature of Monte Carlo simulations can negatively impact the scatter correction.

Scatter simulations using the deterministic radiative transfer equation (RTE) have the potential to provide a noise-free solution with fast simulation speed for scatter compensation. Although scatter simulation using the RTE can be performed in a few seconds using GPU acceleration, discrete ordinate implementations using the RTE can cause a ray effect that, like the noise of Monte Carlo methods, negatively impacts the precision of the simulation. Furthermore, in current many-core processors, a memory bandwidth bottleneck can limit the acceleration of the simulation achievable via parallelization. For example, the acceleration can be limited when the RTE is simulated using a finite-element implementation with an explicit matrix with a very large dimension.

The methods and apparatus described herein use spherical harmonics to calculate the scatter using the RTE to overcome the above-identified challenges.

Figure 1:
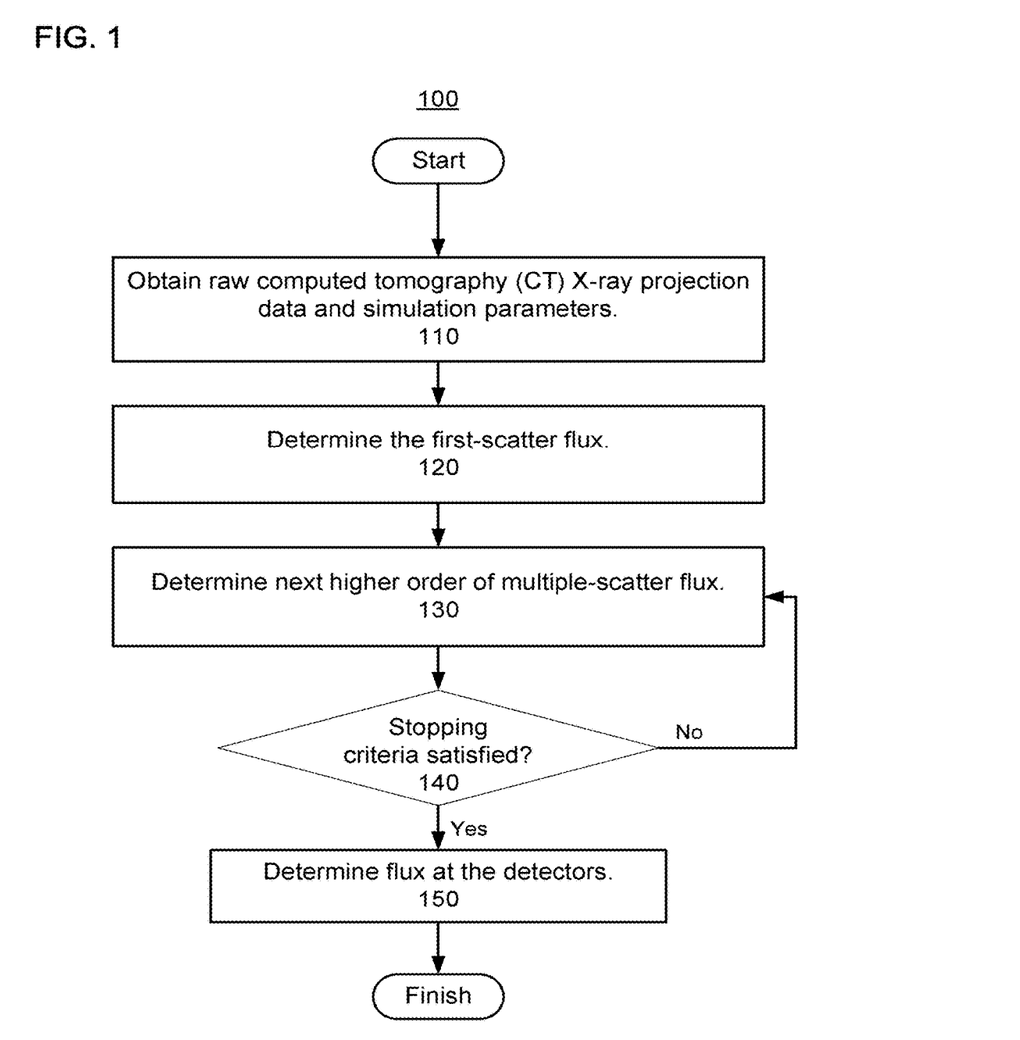
FIG. 1 shows a flow diagram of a method to determine scatter using a three-step integral method for radiative transfer using spherical-harmonic expansions, according to one implementation.
Figure 2:
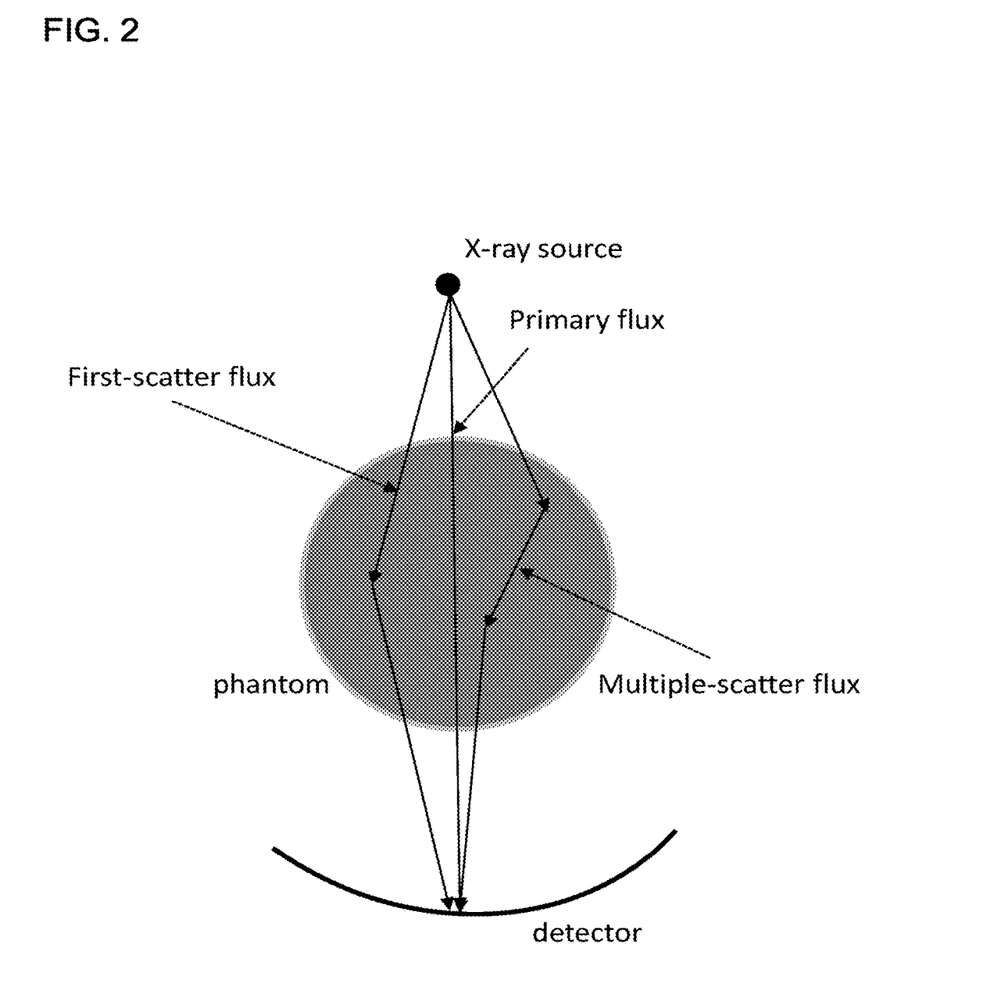
FIG. 2 shows a diagram of first-scatter X-rays and multiple-scatter X-rays detected at a detector, according to one implementation.

Referring now to the drawings, wherein like reference numerals designate identical or corresponding parts throughout the several views, FIG. 1 shows a flow diagram of a method 100 for simulating scatter using a three-step integral formulation of the RTE with spherical harmonics. FIG. 2 shows a diagram of the scatter process in which the primary flux is transmitted with attenuation through an object and detected at a detector. As shown in FIG. 2, the object can be a phantom, or in clinical applications, the object can be a patient. The primary flux includes the X-rays that are not scattered. In addition to the primary flux, the detector also detects first-scatter flux, which includes X-rays that have undergone a single scattering event. Further, the detector also detects multiple-scatter flux, which includes X-rays that have been scattered multiple times.

Scatter can be accurately simulated by including both the first-scatter flux and multi-scatter flux shown in FIG. 2 to represent an accurate physical model. This physical model can be expressed using a radiative transfer equation (RTE), which is given by $$\hat{\Omega} \cdot \nabla \psi(\vec{r}, E, \hat{\Omega}) + \mu(\vec{r}, E, \hat{\Omega})\psi(\vec{r}, E, \hat{\Omega}) =$$
$$\int\int d\hat{\Omega}' dE' f(\vec{r}, E, E', \hat{\Omega} \cdot \hat{\Omega}')\psi(\vec{r}, E', \hat{\Omega}'),$$

subject to the boundary condition $$\psi(\vec{r}_c, E, \hat{\Omega}) = \psi_c(\vec{r}_c, E, \hat{\Omega}), \text{ for } \hat{n} \cdot \hat{\Omega} < 0,$$

wherein $\psi(\vec{r}, E, \hat{\Omega})$ is the specific intensity of photon flux at point $\vec{r}$, E is an energy, and $\hat{\Omega}$ is a unit vector in the direction of propagation for the photon flux. In the boundary condition, the intensity $\psi_c(\vec{r}_c, E, \hat{\Omega})$ depends on the X-ray source and, if a bowtie filter is used to collimator the X-ray source, on the bowtie scattering. Further, the vector $\vec{r}_c$ indicates a point on the surface of the object, $\hat{n}$ is the normal vector to the boundary surface, and $f(\vec{r}, E, E', \hat{\Omega} \cdot \hat{\Omega}')$ is the scatter cross section, which includes both Compton and Rayleigh scattering for X-ray CT. Finally, the variable $\mu(\vec{r}, E)$ represents the total attenuation coefficient for the X-rays at point $\vec{r}$ and energy E.

A method described herein solves the above RTE to obtain a precise scatter solution for CT scatter compensation. This is achieved by first expressing the RTE as an integral equation, which is given by $$\psi(\vec{r}, E, \hat{\Omega}) = \psi_c(\vec{r}_c, E, \hat{\Omega})\exp\left[\int_{\vec{r}_c}^{\vec{r}} d\vec{r}'' \mu(\vec{r}'', E)\right] +$$
$$\int_{\vec{r}_c}^{\vec{r}} d\vec{r}' \int\int d\hat{\Omega}' dE' f(\vec{r}', E, E', \hat{\Omega} \cdot \hat{\Omega}')$$
$$\psi(\vec{r}', E', \hat{\Omega}')\exp\left[-\int_{\vec{r}'}^{\vec{r}} d\vec{r}'' \mu(\vec{r}'', E')\right].$$

As indicated in FIG. 2, the flux can be grouped into three components: (i) the primary flux, (ii) the first-scatter flux, and (iii) the multiple-scatter flux. Method 100 is organized to solve the integral equation representation of the RTE in steps corresponding to the above-identified three respective components of the flux.

The portion of the RTE corresponding to the primary flux can be calculated separately from the portion corresponding to scatter. Further, the portion of the RTE corresponding to scatter lends itself to the application of spherical harmonics, whereas the portion of the RTE corresponding to the primary flux (without scatter) is difficult to expand in terms of spherical harmonics because the primary flux tends to be anisotropic. For example, depending on the geometry of the X-ray beam, the X-ray beam can locally resemble a plane wave. Fortunately, it is not necessary to simultaneously calculate the primary flux with the scatter flux when performing scatter simulation. Accordingly, the RTE can be separated into at least two components (i.e., scatter and primary), and the scatter flux of the RTE can be calculated by $$\psi_s(\vec{r}, E, \hat{\Omega}) = \int_{\vec{r}_c}^{\vec{r}} d\vec{r}' \int\int d\hat{\Omega}' dE' f(\vec{r}', E, E', \hat{\Omega} \cdot \hat{\Omega}')[\psi_s(\vec{r}', E', \hat{\Omega}') +$$
$$\psi_0(\vec{r}', E', \hat{\Omega}')]\exp\left[-\int_{\vec{r}'}^{\vec{r}} d\vec{r}'' \mu(\vec{r}'', E')\right],$$

wherein the primary flux can be calculated as $$\psi_0(\vec{r}, E, \hat{\Omega}) = \psi_c(\vec{r}_c, E, \hat{\Omega})\exp\left[-\int_{\vec{r}_c}^{\vec{r}} d\vec{r}'' \mu(\vec{r}'', E')\right],$$

wherein $\psi_0(\vec{r}', E, \hat{\Omega})$ is the primary flux and $\psi_s(\vec{r}, E, \hat{\Omega})$ is the intensity of the scatter flux. Although the expression for the scatter flux is not a closed-form expression, the scatter flux can be calculated iteratively until convergence, as described below.

In step 110 of method 100, the raw CT projection data is obtained. Further, various other parameters are obtained, including: the X-ray source spectrum, the CT geometry, voxel-based phantom/tissue geometry information, and the scatter cross section and the total attenuation of different materials. For example, the voxel-based phantom/tissue geometry information could be derived from a reconstructed CT image using the uncorrected projection data. Various other input parameters, such as the scatter cross section and total attenuation of different materials, can be derived or extrapolated from a combination of the reconstructed image and prior knowledge about the imaged object (e.g., the imaged object can be a phantom or part of a patient). Additionally, certain of the parameters, such as the X-ray source spectrum and the CT geometry, can be measured beforehand during calibrations or obtained from known specifications of the CT apparatus.

In step 120 of method 100, the first-scatter flux is calculated. Similar to the primary-flux calculation, the first-scatter flux is also obtained directly from X-ray CT system, and, therefore, calculating the first-scatter flux using a spherical-harmonic expansion is also difficult. Nevertheless, the first-scatter flux can be calculated by a discretized integral formula, which is given by $$\psi_1(\vec{r}, E, l, m) = \int\int\int d^3\vec{r}' \exp\left[-\int_{\vec{r}'}^{\vec{r}} d\vec{r}'' \mu(\vec{r}'', E)\right] \frac{1}{|\vec{r}-\vec{r}'|^2} Y_{lm}^*(\hat{\Omega}) \times$$
$$\int dE' f(\vec{r}', E, E', \hat{\Omega} \cdot \hat{\Omega}')\psi_c(\vec{r}_c, E', \hat{\Omega}')\exp\left[-\int_{\vec{r}_c}^{\vec{r}'} d\vec{r}'' \mu(\vec{r}'', E')\right],$$

wherein $Y^*_{lm}(\hat{\Omega})$ is the complex conjugation of a spherical harmonic function of degree l and order m, and $\psi_1(\vec{r}, E, lm)$ is the intensity of the first-scatter flux in the spherical-harmonics domain. The spherical harmonics can be given by $$Y_{lm}(\hat{\Omega}) = Y_{lm}(\theta, \phi)$$
$$= N\exp(im\phi)P_l^m(\cos\theta),$$

wherein $Y_{lm}(\hat{\Omega})$ a spherical harmonic function of degree l and order m, $P_l^m$ is an associated Legendre polynomial, N is a normalization constant, and $\theta$ and $\phi$ represent colatitude and longitude, respectively. The number of spherical harmonics used to approximate the first-scatter flux can depend on the material component and scatter cross-section at the point $\vec{r}'$ and on the type of scattering (e.g., Compton and Raleigh scattering).

Different materials, such as bone and water, have different scattering cross-sections with different angular dependence, depending on their atomic constituents. Also, the magnitude of the scatter cross-section can depend on the density of material components at the point $\vec{r}'$. Thus, the physical model, such as the physical model shown in FIG. 2, can be decomposed into material components using a material decomposition to determine the density of various material components as a function of position, and the position-dependent scatter cross-section can be obtained from the spatial density map of the material components. The position dependent cross-section can be obtained as a linear superposition of the coefficients of the material components and previously computed normalized scatter cross-sections for the material components. The material decomposition can be performed using dual-energy CT, or using a threshold and region-growing method that infers regions corresponding to material components by the attenuation of the voxels (e.g., voxels having a attenuation value above a predefined threshold in Hounsfield Units are determined to be bone).

X-ray scattering is dominated by Compton scattering, which tends to be more isotropic than other scattering mechanisms such as Raleigh scattering. Accordingly, for common materials such as bone and water, an accurate approximation to the Compton scattering of X-rays can be achieved with relatively few spherical harmonics. The number of spherical harmonics applied in method 100 can be predetermined empirically, or determined during the execution of method 100 using a convergence criterion for the accuracy of the approximation.

In step 130 of method 100, the higher-order scatter terms are calculated. Whereas the first-scatter flux includes only X-ray photons that have been scattered one time, the $k^{th}$-order scatter term includes X-ray photons that have been scattered k times. After the first-scatter flux is calculated, the flux of multiple scatters can be calculated using a discretized integral spherical harmonics formula, which is given by $$\psi_s^{k+1}(\vec{r}, E, l, m) = \psi_1(\vec{r}, E, l, m) +$$

$$\int\int\int d^3\vec{r}' \exp\left[-\int_{\vec{r}'}^{\vec{r}} d\vec{r}'' \mu(\vec{r}'', E')\right] \frac{1}{|\vec{r}-\vec{r}'|^2} Y_{lm}^*(\hat{\Omega}) \times$$

$$\sum_{E'}\sum_{\bar{l}} f(\vec{r}', E, E', \bar{l}) \sum_{\bar{m}} Y_{\bar{l}\bar{m}}(\hat{\Omega}) \psi_s^k(\vec{r}', E', \bar{l}, \bar{m}),$$

wherein $\psi_s^{k+1}(\vec{r}, E, lm)$ and $\psi_s^k(\vec{r}', E', \bar{l}\bar{m})$ are the intensity of the flux for multiple scatter including all scatter events up to order k+1 and order k respectively and $f(\vec{r}', E, E', \bar{l})$ is the $\bar{l}$-th coefficient when the scatter cross-section is expanded using the Legendre polynomials. By defining $$A = \int\int\int d^3\vec{r}' \exp\left[-\int_{\vec{r}'}^{\vec{r}} d\vec{r}'' \mu(\vec{r}'', E')\right]$$

$$\frac{1}{|\vec{r}-\vec{r}'|^2} Y_{lm}^*(\hat{\Omega}) \sum_{E'}\sum_{\bar{l}} f(\vec{r}', E, E', \bar{l}) \sum_{\bar{m}} Y_{\bar{l}\bar{m}}(\hat{\Omega}),$$

the above-defined iterative formula can be more simply expressed as $$\psi_s^{k+1} = A\psi_s^k + \psi_1.$$

In step 140 of method 100, a stopping criteria is assessed to determine whether approximation up to order k is sufficiently accurate. i.e., whether scattering accounted for by the above-defined iterative multiple-scatter calculation when calculated up to order k provides an adequately accurate representation of the scatter. For example, the stopping criteria can be satisfied when $$\frac{|\psi_s^{k+1} - \psi_s^k|}{\psi_s^k} \leq \epsilon,$$

wherein $\epsilon$ is a predefined threshold. Further, the stopping criteria can be satisfied when a maximum value for k (i.e., a maximum number of iterations) has been reached. If the stopping criteria are satisfied, then method 100 proceeds from step 140 to step 150. Otherwise, step 130 is repeated for the next higher order of multiple scattering.

In step 150 of method 100, the flux at the detector is determined. In certain implementations, the incident flux on the detectors is affected by anti-scatter grids, such that the X-rays actually detected at the detectors differ from the incident flux. Accordingly, in step 150, the effect of the anti-scatter grid on the first-scatter flux and the multiple-scatter flux is determined. The anti-scatter grids are arranged, as much as possible, to limit and prevent scatter from reaching the detectors. Accordingly, the effect of properly arranged anti-scatter grids on the incident scatter flux can be significant.

After calculating the flux of multiple scatters, the scatter flux intensity $\Phi_s(\vec{r}_D, E)$ on the detectors can be calculated by $$\Phi_s(\vec{r}_D, E) = \int\int\int d^3r' \frac{R_{ASG}(E, \hat{\Omega})}{|\vec{r}_D - \vec{r}'|^2}$$

$$\int dE' \sum_{l',m'} f(\vec{r}', E, E', l') Y_{l'm'}(\hat{\Omega}) \psi_s(\vec{r}', E', l', m') \times$$

$$\exp\left[-\int_{\vec{r}'}^{\vec{r}_c} d\vec{r}'' \mu(\vec{r}'', E')\right] + \int\int\int d^3r' R_{ASG}(E, \hat{\Omega}) \frac{1}{|\vec{r}_D - \vec{r}'|^2}$$

$$\int dE' f(\vec{r}', E, E', \hat{\Omega} \cdot \hat{\Omega}') \times \psi_c(\vec{r}_c, E, \hat{\Omega}) \exp\left[-\int_{\vec{r}_0}^{\vec{r}'} d\vec{r}'' \mu(\vec{r}'', E)\right]$$

$$\exp\left[-\int_{\vec{r}'}^{\vec{r}_c} d\vec{r}'' \mu(\vec{r}'', E)\right],$$

wherein $R_{ASG}(E, \hat{\Omega})$ is the factor accounting for the effects of the anti-scatter grid. $R_{ASG}(E, \hat{\Omega})$ is dependent only on the arrangement and configuration of the anti-scatter grids, and, therefore, can be precomputed and stored for the configuration of the anti-scatter grids. $R_{ASG}(E, \hat{\Omega})$ can be precomputed using any known method, including any known analytical approach, Monte Carlo method, or RTE method. When no anti-scatter grid is used, $R_{ASG}(E, \hat{\Omega})$ can be replaced by a constant value of one.

In certain implementations, the attenuation integrals $$\exp\left[-\int_{\vec{r}'}^{\vec{r}} d\vec{r}'' \mu(\vec{r}'', E')\right]$$

can be computed more quickly using a material decomposition to calculate the attenuation due to a first and a second material components. This makes method 100 more efficient by the computational resources required to calculate the energy-dependent attenuation between voxels $$\left(\text{i.e., } \exp\left[-\int_{\vec{r}'}^{\vec{r}} d\vec{r}'' \mu(\vec{r}'', E)\right]\right),$$

which, when calculating the flux of multiple scatters, can use significant computational resources and time. According to the material decomposition method, the attenuation coefficient at each location within the physical model can be divided into multiple attenuation coefficients corresponding to the constituent material components. For example, the attenuation coefficient can be divided as $$\mu(\vec{r}, E) = c_w(\vec{r}) \mu_w(E) + c_b(\vec{r}) \mu_b(E)$$

wherein $c_w(\vec{r})$ and $c_b(\vec{r})$ are the decomposed coefficient corresponding to water ($\mu_w(E)$) and bone ($\mu_b(E)$). Thus, the attenuation calculation can be reduced using material components to yield $$\int_{\vec{r}'}^{\vec{r}} d\vec{r}'' \mu(\vec{r}'', E) = \int_{\vec{r}'}^{\vec{r}} c_w(\vec{r}'') d\vec{r}'' \mu_w(E) + \int_{\vec{r}'}^{\vec{r}} c_b(\vec{r}'') d\vec{r}'' \mu_b(E).$$

Using the above material-decomposition formulation of the attenuation calculation, the attenuation calculation can be calculated using only two basis line integrals to obtain the line integrals at any energy. Additionally, the integrals $$\int_{\vec{r}'}^{\vec{r}} c_w(\vec{r}'') d\vec{r}'' \text{ and } \int_{\vec{r}'}^{\vec{r}} c_b(\vec{r}'') d\vec{r}''$$

can be calculated once and a look-up table can be generated to further accelerate future calculations of the attenuation along various rays.

The methods described herein solve a radiative transfer equation for scatter simulation of CT. Compared to other methods of simulating scatter, the methods described herein provide several advantages over other methods. For example, compared to Monte Carlo based methods, which impose noise due to their statistical nature, the methods described herein can provide noise-free solutions. Thus, without sacrificing precision and increasing the noise, the methods described herein provide a fast simulation algorithm for scatter correction.

Compared to the methods that do not solve the RTE problem by separating the problem into three parts (i.e., the primary flux, the first-scatter flux, and the multiple-scatter flux), the methods described herein advantageously separate the RTE problem into sub-problems that are amenable to solution using spherical harmonics and sub-problems that are not. The X-rays from the X-ray source are not amenable to being expanded in terms of spherical harmonics due to their anisotropic nature. Thus, compared to other methods, the three-step simulation framework of the methods described herein avoids direct spherical-harmonic expansion of the X-ray source, but use spherical-harmonic expansion for the multiple-scatter flux where such expansion provides advantages. Accordingly, computational precision and efficiency are improved.

Further, the methods described herein are an improvement over other methods because the use of spherical harmonics methods can effectively avoid the ray effect, which happens in discrete ordinate methods. In addition, in X-ray CT spectrum, scatter is dominated by Compton scattering, as discussed above, and the scatter cross-section is relatively isotropic, in contrast to other portions of the electromagnetic spectrum. Accordingly, fast simulations with precise solutions can be obtained due to spherical harmonics expansion with relatively few orders of spherical harmonics.

Moreover, in contrast to finite-element methods, which generally require explicit matrix storage, the methods described herein can be performed using parallel computational processors. Using finite-element methods, the dimension of unknown variables in the RTE simulation is very large because the flux is a function of space, angle, and energy. Consequently, acceleration of an RTE simulation is limited due to explicit matrix storage with very large dimension. In contrast, the integral spherical harmonics format of the methods described herein does not need explicit matrix storage. Accordingly, the methods described herein can potentially to achieve computational acceleration, especially by using many-core processors.

Finally, one challenge to performing physical scatter simulation is that the simulation can require significant computational resources and time. Accordingly, the methods described herein use material decomposition on the attenuation coefficient to improve the functioning of a computer when performing the scatter simulations. Further, the proposed look-up table of the material-decomposed attenuation coefficients can further accelerate the simulation by eliminating repeated attenuation calculations for each iteration of the multiple scatter calculation.

Figure 3:
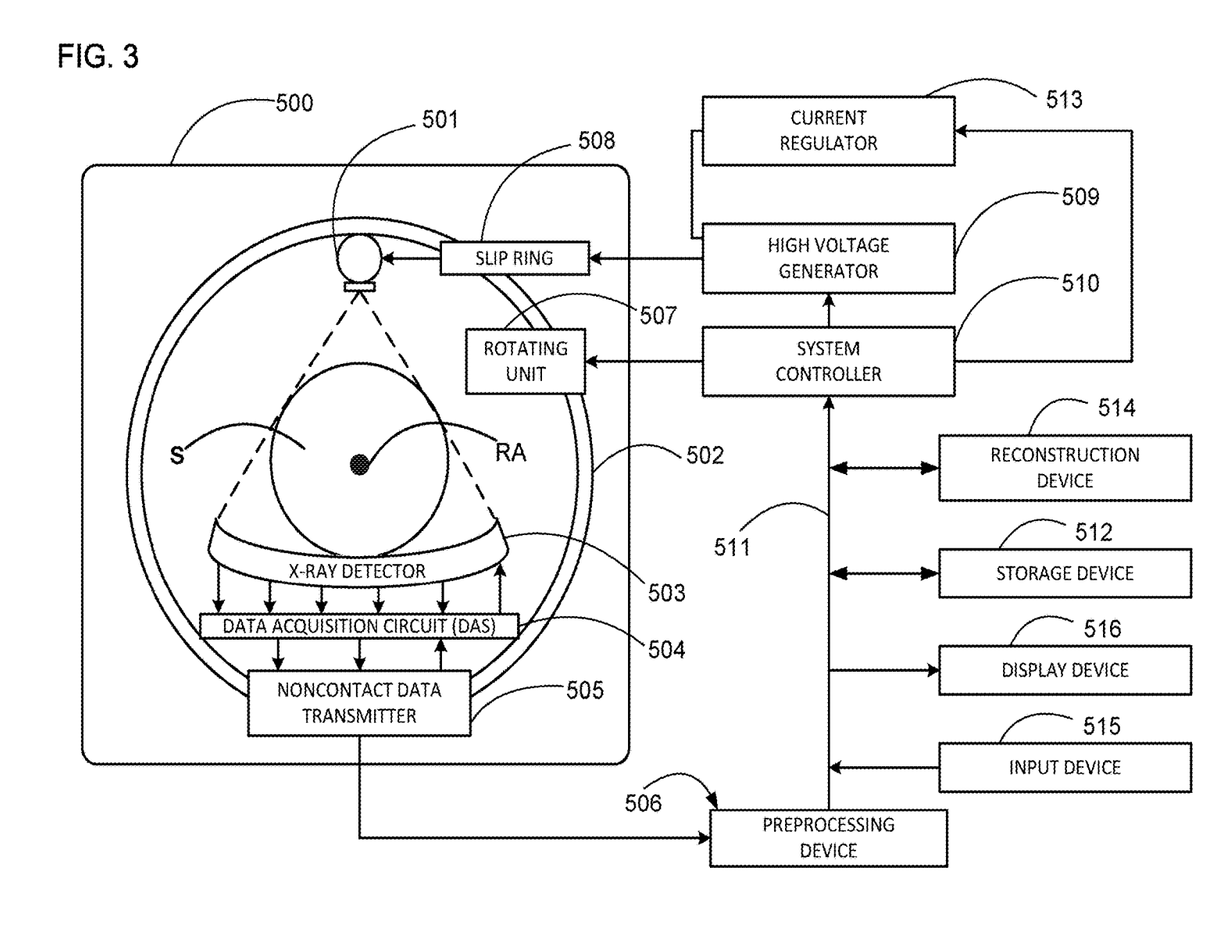
FIG. 3 shows a schematic of an implementation of a CT scanner.

FIG. 3 illustrates an implementation of the radiography gantry included in a CT apparatus or scanner. As shown in FIG. 3, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA. A rotating unit 507 rotates the annular frame 502 at a high speed, such as 0.4 sec/rotation, while the object OBJ is being moved along the axis RA into or out of the illustrated page.

The first embodiment of an X-ray computed tomography (CT) apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate type, which is currently the mainstream, will be exemplified.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal. The X-ray detector 503 and the DAS 504 are configured to handle a predetermined total number of projections per rotation (TPPR).

The above-described data is sent to a preprocessing device 506, which is housed in a console outside the radiography gantry 500 through a non-contact data transmitter 505. The preprocessing device 506 performs certain corrections, such as sensitivity correction on the raw data. A memory 512 stores the resultant data, which is also called projection data at a stage immediately before reconstruction processing. The memory 512 is connected to a system controller 510 through a data/control bus 511, together with a reconstruction device 514, input device 515, and display 516. The system controller 510 controls a current regulator 513 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 501 and the X-ray detector 503 are diametrically mounted on the annular frame 502 and are rotated around the object OBJ as the annular frame 502 is rotated about the rotation axis RA. In the fourth-generation geometry system, the detectors are fixedly placed around the patient and an X-ray tube rotates around the patient. In an alternative embodiment, the radiography gantry 500 has multiple detectors arranged on the annular frame 502, which is supported by a C-arm and a stand.

The memory 512 can store the measurement value representative of the irradiance of the X-rays at the X-ray detector unit 503. Further, the memory 512 can store a dedicated program for executing the CT image reconstruction, material decomposition, and scatter estimation and corrections methods including method 100 discussed herein.

The reconstruction device 514 can execute the method 100 discussed herein. Further, reconstruction device 514 can execute pre-reconstruction processing image processing such as volume rendering processing and image difference processing as needed.

The pre-reconstruction processing of the projection data performed by the preprocessing device 506 can include correcting for detector calibrations, detector nonlinearities, and polar effects, for example.

Post-reconstruction processing performed by the reconstruction device 514 can include filtering and smoothing the image, volume rendering processing, and image difference processing as needed. The image reconstruction process can be performed using filtered back projection, iterative image reconstruction methods, or stochastic image reconstruction methods. The reconstruction device 514 can use the memory to store, e.g., projection data, reconstructed images, calibration data and parameters, and computer programs.

The reconstruction device 514 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 512 can be non-volatile, such as ROM, EPROM, EEPROM or FLASH memory. The memory 512 can also be volatile, such as static or dynamic RAM, and a processor, such as a microcontroller or microprocessor, can be provided to manage the electronic memory as well as the interaction between the FPGA or CPLD and the memory.

Alternatively, the CPU in the reconstruction device 514 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 516. The display 516 can be an LCD display, CRT display, plasma display, OLED, LED or any other display known in the art.

The memory 512 can be a hard disk drive, CD-ROM drive, DVD drive, FLASH drive, RAM, ROM or any other electronic storage known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:
1. An apparatus, comprising:
 circuitry configured to
  obtain projection data representing an intensity of X-ray radiation detected at a plurality of detector elements,
  obtain a model of an object between an X-ray source generating the X-ray radiation and the plurality of detector elements, the model representing a spatial distribution of material components of the object, determine, using the model and a radiative transfer equation, scattered X-ray data representing an intensity of scattered X-ray radiation detected at the plurality of detector elements, the radiative transfer equation being expressed as an integral equation including a first portion corresponding to a primary flux and a second portion corresponding to a scatter flux, the scattered X-ray data being determined by integrating an attenuation from the X-ray source to a detection location or a first scatter location to calculate the first portion for generation of the primary flux, and iteratively calculating a multiple-scatter flux from a first order scatter calculated based on the primary flux at the first scatter location, using position dependent cross-sections and spherical-harmonic components to calculate the second portion for generation of the scatter, correct the projection data based on the scattered X-ray data to obtain scatter corrected projection data, and reconstruct an image of the object from the scatter-corrected projection data; and a display configured to display the reconstructed image of the object.

2. The apparatus according to claim 1, wherein the circuitry is further configured to iteratively calculate the multiple-scatter flux by iteratively updating the multiple-scatter flux, which is decomposed into a plurality of multiple-scatter spherical-harmonic components, by integrating products of respective spherical-harmonic components of a previous iteration of the multiple-scatter flux at a scatter location of the previous iteration with corresponding spherical-harmonic components of the predefined scatter cross-section at a scatter location of a next iteration to generate the multiple-scatter flux of the next iteration, wherein the multiple-scatter flux of a first iteration is the first-scatter flux and a scatter location of the first iteration is the first scatter location.

3. The apparatus according to claim 2, wherein the circuitry is further configured to calculate the scattered X-ray data by the iteratively updating of the multiple-scatter flux using spherical-harmonic components of the predefined scatter cross-section that are obtained by using a Legendre polynomial to expand the predefined scatter cross-section.

4. The apparatus according to claim 2, wherein the circuitry is further configured to calculate the scattered X-ray data by the updating of the multiple-scatter flux, including integrating an attenuation from the scatter location of the previous iteration to the scatter location of the next iteration.

5. The apparatus according to claim 1, wherein the circuitry is further configured to calculate the scattered X-ray data by the integrating of the attenuation from the X-ray source to the detection location or the first scatter location, including a material decomposition of the attenuation into a plurality of material components.

6. The apparatus according to claim 5, wherein the circuitry is further configured to calculate the scattered X-ray data by the integrating of the attenuation from the X-ray source to the detection location or the first scatter location, including precomputing the plurality of material attenuation components and storing the plurality of material attenuation components in a memory.

7. The apparatus according to claim 1, wherein the circuitry is further configured to determine the predefined scatter cross-sections at respective scatter locations of the iterations of the iteratively updating of the multiple-scatter flux using corresponding scatter locations on the spatial distribution of the material components of the object represented by the model and predetermined scatter cross-sections of the material components of the object.

8. The apparatus according to claim 1, wherein the circuitry is further configured to obtain the model of the object by correcting scatter in the projection data using a kernel-based method to generate corrected projection data, reconstructing a computed tomography image of the object to generate the model of the object, and performing material decomposition to generate the material components of the object for the model.

9. The apparatus according to claim 2, wherein the circuitry is further configured to calculate the scattered X-ray data by correcting the first-scatter flux at the plurality of detector elements to account for an effect of an anti-scatter grid, and correcting the multiple-scatter flux at the plurality of detector elements to account for the effect of the anti-scatter grid.

10. The apparatus according to claim 1, further comprising:

a gantry including a rotating member;

the X-ray source radiating X-rays, the X-ray source fixed to the rotating member; and the plurality of detector elements fixed to the rotating member and arranged diametrically opposed to the X-ray source, wherein the obtaining of the projection data is performed by detecting, at the plurality of detector elements, X-ray radiation from the X-ray source to generate the projection data.

11. An apparatus, comprising:

circuitry configured to obtain projection data representing an intensity of X-ray radiation detected at a plurality of detector elements, obtain a model of an object between an X-ray source generating the X-ray radiation and the plurality of detector elements, the model representing a spatial distribution of material components of the object, determine, using the model and a radiative transfer equation, scattered X-ray data representing an intensity of scattered X-ray radiation detected at the plurality of detector elements, the radiative transfer equation being expressed as an integral equation including a first portion corresponding to a primary flux and a second portion corresponding to a scatter flux, the scattered X-ray data being determined by integrating an attenuation from the X-ray source to a detection location or a first scatter location to calculate the first portion for generation of the primary flux, and iteratively calculating a multiple-scatter flux from a first order scatter calculated based on the primary flux at the first scatter location, using position dependent cross-sections and spherical-harmonic components to calculate the second portion for generation of the scatter, correct the projection data based on the scattered X-ray data to obtain scatter-corrected projection data, and reconstruct an image of the object from the scatter corrected projection data; and a display configured to display the reconstructed image of the object.

12. A method, comprising:

obtaining projection data representing an intensity of X-ray radiation detected at a plurality of detector elements, obtaining a model of an object between an X-ray source generating the X-ray radiation and the plurality of detector elements, the model representing a spatial distribution of material components of the object, determining, using the model and a radiative transfer equation, scattered X-ray data representing an intensity of scattered X-ray radiation detected at the plurality of detector elements, the radiative transfer equation being expressed as an integral equation including a first portion corresponding to a primary flux and a second portion corresponding to a scatter flux, by integrating a radiative transfer equation, wherein the determining of the scattered X-ray data includes integrating an attenuation from the X-ray source to a detection location or a first scatter location to calculate the first portion for generation of the primary flux, and iteratively calculating a multiple-scatter flux from a first order scatter calculated based on the primary flux at the first scatter location, using position dependent cross-sections and spherical-harmonic components to calculate the second portion for generation of the scatter correcting the projection data based on the scattered X-ray data to obtain scatter corrected projection data, and reconstructing an image of the object from the scatter corrected projection data, and displaying the reconstructed image of the object.

13. The method according to claim 12, wherein the iteratively calculating the multiple-scatter flux includes iteratively updating the multiple-scatter flux, which is decomposed into a plurality of multiple-scatter spherical-harmonic components, by integrating products of respective spherical-harmonic components of a previous iteration of the multiple-scatter flux at a scatter location of the previous iteration with corresponding spherical-harmonic components of the predefined scatter cross-section at a scatter location of a next iteration to generate the multiple-scatter flux of the next iteration, wherein the multiple-scatter flux of a first iteration is the first-scatter flux and a scatter location of the first iteration is the first scatter location.

14. The method according to claim 13, wherein the iteratively updating of the multiple-scatter flux is performed using spherical-harmonic components of the predefined scatter cross-section that are obtained by using a Legendre polynomial to expand the predefined scatter cross-section.

15. The method according to claim 13, wherein the updating of the multiple-scatter flux includes integrating an attenuation from the scatter location of the previous iteration to the scatter location of the next iteration.

16. The method according to claim 12, wherein the integrating of the attenuation from the X-ray source to the detection location or the first scatter location includes a material decomposition of the attenuation into a plurality of material components.

17. The method according to claim 16, wherein the integrating of the attenuation from the X-ray source to the detection location or the first scatter location includes pre-computing the plurality of material attenuation components and storing the plurality of material attenuation components in a memory.

18. The method according to claim 12, wherein the obtaining of the model of the object further includes correcting scatter in the projection data using a kernel-based method to generate corrected projection data, reconstructing a computed tomography image of the object to generate the model of the object, and performing material decomposition to generate the material components of the object for the model.

19. The method according to claim 13, wherein the determining of the scattered X-ray data further includes correcting the first-scatter flux at the plurality of detector elements to account for an effect of an anti-scatter grid, and correcting the multiple-scatter flux at the plurality of detector elements to account for the effect of the anti-scatter grid.

20. A non-transitory computer readable storage medium including executable instructions, wherein the instructions, when executed by circuitry, cause the circuitry to perform the method according to claim 12.

* * * * *